(12) United States Patent
Beumer et al.

(10) Patent No.: US 11,136,277 B2
(45) Date of Patent: Oct. 5, 2021

(54) PROCESS FOR THE PRODUCTION OF BETA-SPRINGENE

(71) Applicant: DSM IP ASSETS B.V., Heerlen (NL)

(72) Inventors: Raphael Beumer, Kaiseraugst (CH); Werner Bonrath, Kaiseraugst (CH); Marc-André Mueller, Kaiseraugst (CH); Bettina Wüestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/645,589

(22) PCT Filed: Sep. 13, 2018

(86) PCT No.: PCT/EP2018/074747
§ 371 (c)(1),
(2) Date: Mar. 9, 2020

(87) PCT Pub. No.: WO2019/057599
PCT Pub. Date: Mar. 28, 2019

(65) Prior Publication Data
US 2020/0277244 A1    Sep. 3, 2020

(30) Foreign Application Priority Data
Sep. 22, 2017 (EP) ..................... 17192636

(51) Int. Cl.
*C07C 1/213* (2006.01)
(52) U.S. Cl.
CPC .......... *C07C 1/213* (2013.01); *C07C 2531/02* (2013.01); *C07C 2531/24* (2013.01)
(58) Field of Classification Search
None
See application file for complete search history.

(56) References Cited

PUBLICATIONS

International Search Report for PCT/EP2018/074747, dated Nov. 26, 2018, 4 pages.
Burger et al., "Mammalian pheromone studies, IV*. Terpenoid Compounds and Hydroxy Esters from the Dorsal Gland of the Springbok, Antidorcas marsupialis", Journal of Biosciences, Apr. 1, 1981, vol. 36, No. 3-4, pp. 340-343.
Tsuji et al., "Formation of a terminal conjugated diene system by the palladium catalyzed elimination reactions of allylic acetates and phenyl ethers", Tetrahedron Letters, vo. 19, No. 24, Jan. 1, 1978, pp. 2075-2078.
Hutchins et al., "Reductive displacement of allylic acetates by hydride transfer via catalytic activation by palladium(0) complexes", Tetrahedron Letters, vol. 21, No. 1, Jan. 1, 1980, pp. 27-30
Andersson et al., "Mechanism of the Palladium-Catalyzed Elimination of Acetic Acid from Allylic Acetates", Organometallics, vol. 14, No. 1, Jan. 1, 1995, pp. 1-2.

*Primary Examiner* — Philip Y Louie
*Assistant Examiner* — Alyssa L Cepluch
(74) *Attorney, Agent, or Firm* — Nixon & Vanderhye P.C.

(57) ABSTRACT

The present invention relates to a process for the production of β-springene of formula (I) wherein a compound of formula (II) is heated in the presence of a catalyst.

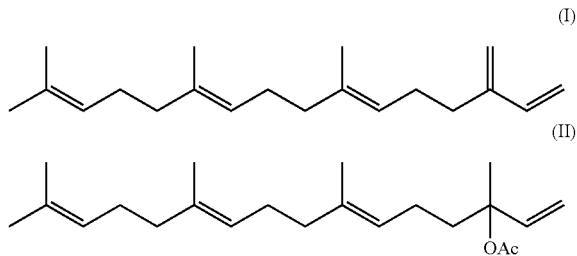

2 Claims, No Drawings

PROCESS FOR THE PRODUCTION OF BETA-SPRINGENE

This application is the U.S. national phase of International Application No. PCT/EP2018/074747 filed 13 Sep. 2018, which designated the U.S. and claims priority to EP Patent Application No. 17192636.3 filed 22 Sep. 2017, the entire contents of each of which are hereby incorporated by reference.

The present invention relates to a new process to produce β-springene.

β-Springene, which is the compound of formula (I)

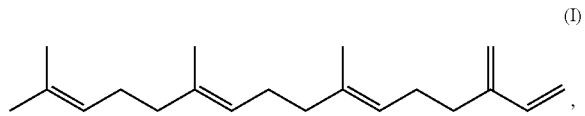 [SMILES: C=CC(=C)CC/C=C(\C)CC/C=C(\C)CCC=C(C)C]
(I)

is a compound, which can be found in the sex attractant secretion of the springbok (a South African gazelle).

β-Springene is a very useful compound in the field of isoprenoid chemistry.

Due to the importance of β-springene, there is always a need for an efficient process of production.

The goal of the present invention was to find an improved synthesis for β-springene.

It was surprisingly found that β-springene can be produced from geranyl linalyl acetate in good yields.

The reaction scheme is the following:

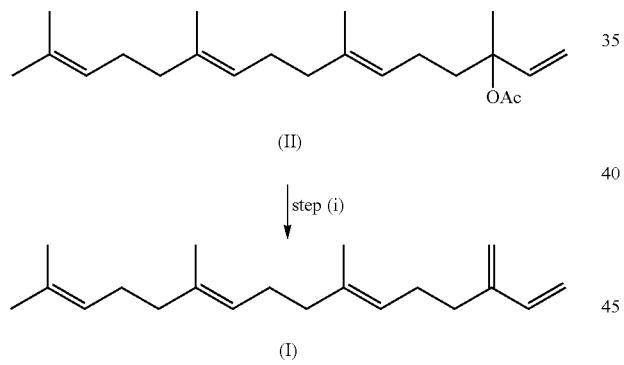

The starting material (compound of formula (II)) can be obtained commercially or it can be produced starting from the compound of formula (III)

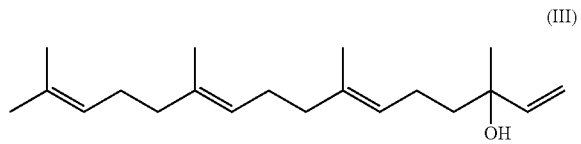 [SMILES: C=CC(C)(O)CC/C=C(\C)CC/C=C(\C)CCC=C(C)C]
(III)

The synthesis of the compound of formula (II) is known from literature (i.e. from M. Grinco et al., Helv. Chim. Acta 2008, 91(2), 249-258; A. K. Bakkestuen, Organic and Biomolecular Chemistry 2005, 3(6), 1025-1033).

Step (i)

In step (i) the compound of formula (II) is used as a starting material. The reaction of step (i) is usually carried out in at least one solvent. Suitable solvents are polar aprotic solvents, such as dimethyl sulfoxide (DMSO), carbonates, esters, and ketones.

The reaction of step (i) is usually carried out at elevated temperature (usually above 30° C., usually in range of 30° C.-80° C.).

The reaction of step (i) is usually carried out under an inert gas atmosphere.

The reaction of step (i) is an elimination reaction which is usually and preferably carried out in the presence of a catalyst.

The reaction is performed preferred in presence of a catalyst which is a heterocylic organic base and a metal complex. Useful organic bases are:

1,8-Diazabicyclo[5.4.0]undec-7-ene (DBU), Tröger base (2,8-Dimethyl-6H,12H-5,11-methanodibenzo[b,f][1,5]diazocine), 1,4-Diazabicyclo[2.2.2]octane (DABCO).

Preferred metals are of Ni, Pd, and Pt.

Preferred metal complexes are $Pd(PPh_3)_4$, $Ni(PPh_3)_4$, $Pt(PoTol_3)_4$, $Pt(PPh_3)_4$, $Ni(PoTol_3)_4$, $Pd(PoTol_3)_4$, $Pd(Palkyl_3)_4$, $Ni(Palkyl_3)_4$, $Pd(Palkyl_3)_4$, $Ni(OPPh_3)_4$, $Pd(OPPh_3)_4$, $Pt(OPPh_3)_4$, wherein alkyl means $C_1$-$C_6$-alkyl, which can be linear or branched. $PoTol_3$ is an abbreviation of tris(o-tolyl)phosphine.

The obtained product (compound of formula (I)) can then be isolated and purified according to known methods.

The yield which can be achieved by the process according to the present invention are good.

β-Springene can be used as such or as mentioned above as a building block in the field of terpenoid chemistry.

The following examples serve to illustrate the invention. The temperature is given in ° C. and all percentages are related to the weight.

EXAMPLES

Example 1

Elimination of Acetic Acid from Geranyl Linayl Acetate

Under inert gas atmosphere, 1.4 mmol of geranyl linalyl acetate ((6E,10E)-3,7,11,15-tetramethylhexadeca-1,6,10,14-tetraen-3-yl acetate) were dissolved in 2.9 ml of anhydrous DMSO. At room temperature, subsequently 2.9 mmol (2.00 eq.) of DBU and 0.100 mmol (7 mol %) of $Pd(PPh_3)_4$ were added to the stirred solution. Then, the reaction mixture was heated to 60° C. (oil-bath temperature) and stirred for 2 hours. After that, the reaction mixture was cooled to room temperature, and diluted with ethyl acetate (100 ml). The organic solution was subsequently washed with water (2×100 ml) and brine (100 ml). The aqueous phase was re-extracted with ethyl acetate (3×100 ml). The combined organic layers were dried over $Na_2SO_4$, filtered, and concentrated under reduced pressure. The crude product (8.27 g) was obtained as a mixture of β- and α-springene in a ratio of 4:1. Quantitative analysis of the crude product showed 50.4% purity for β-springene (77% yield) and 13.0% purity for α-springene (20% yield). The crude material was purified by column chromatography ($SiO_2$, pentane).

Example 2

Under inert gas atmosphere, geranylgeranyl acetate (1.3 mmol) was dissolved in anhydrous DMSO (2.5 ml). With stirring DBU (2 eq.) and Pd(PPh3)4 (7 mol %) were added and the reaction mixture was warmed to 60° C. within 15 min. After 3 hours reaction time, the mixture was cooled to room temperature and transferred into a separation funnel with 20 ml of ethyl acetate. The organic phase was washed with water (2×20 ml) and brine (20 ml). The aqueous layers were extracted with ethyl acetate (3×20 ml). The combined organic layers were dried over MgSO4 and concentrated under reduced pressure. The product was obtained as an isomeric mixture of β- and α-springene (7:3) in 66% yield.

When using geranylgeraniol or geranyl linallol as starting material, no conversion was observed under the same reaction conditions.

The invention claimed is:
1. A process to produce a compound of formula (I):

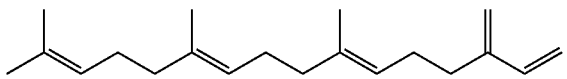

(I)

wherein the process comprises heating a compound of formula (II) at a temperature of 30° C.-80° C.:

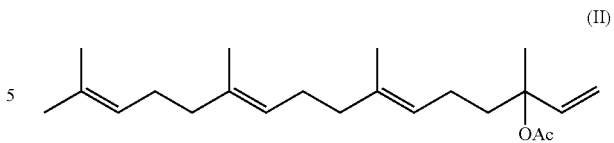

(II)

in the presence of a catalyst and in the presence of dimethyl sulfoxide (DMSO) to thereby form the compound of formula (I), and wherein the catalyst is selected from the group consisting of 1,8-Diazabicyclo[5.4.0]undec-7-ene (DBU), Tröger base (2,8-Dimethyl-6H,12H-5,11-methanodibenzo[b,f][1,5]diazocine), 1,4-Diazabicyclo[2.2.2]octane (DABCO), Pd(PPh$_3$)$_4$, Ni(PPh$_3$)$_4$, Pt(PoTol$_3$)$_4$, Pt(PPh$_3$)$_4$, Ni(PoTol$_3$)$_4$, Pd(PoTol$_3$)$_4$, Pd(Palkyl$_3$)$_4$, Ni(Palkyl$_3$)$_4$, Pd(Palkyl$_3$)$_4$, Ni(OPPh$_3$)$_4$, Pd(OPPh$_3$)$_4$, and Pt(OPPh$_3$)$_4$, wherein alkyl is a linear or branched C$_1$-C$_6$-alkyl.

2. The process according to claim 1, wherein the process is carried out under an inert gas atmosphere.

* * * * *